US010314784B2

(12) United States Patent
Haeberlin et al.

(10) Patent No.: US 10,314,784 B2
(45) Date of Patent: Jun. 11, 2019

(54) COMPOSITIONS OF GLYCOPYRRONIUM SALT FOR INHALATION

(71) Applicants: Barbara Haeberlin, Munchenstein (DE); Frank Stowasser, Murg (DE); Wolfgang Wirth, Arisdorf (CH); Anton Baumberger, Binningen (CH); Stephan Abel, Weil am Rhein (DE); Sebastian Kaerger, Riehen (CH); Thomas Kieckbusch, Lorrach (DE)

(72) Inventors: Barbara Haeberlin, Munchenstein (DE); Frank Stowasser, Murg (DE); Wolfgang Wirth, Arisdorf (CH); Anton Baumberger, Binningen (CH); Stephan Abel, Weil am Rhein (DE); Sebastian Kaerger, Riehen (CH); Thomas Kieckbusch, Lorrach (DE)

(73) Assignee: Novartis AG, Basel (CH)

( * ) Notice: Subject to any disclaimer, the term of this patent is extended or adjusted under 35 U.S.C. 154(b) by 308 days.

(21) Appl. No.: 14/960,472

(22) Filed: Dec. 7, 2015

(65) Prior Publication Data

US 2016/0081934 A1    Mar. 24, 2016

Related U.S. Application Data

(63) Continuation of application No. 14/692,033, filed on Apr. 21, 2015, now abandoned, which is a continuation of application No. 13/271,689, filed on Oct. 12, 2011, now abandoned, which is a continuation of application No. 12/305,263, filed as application No. PCT/EP2007/005744 on Jun. 28, 2007, now abandoned.

(30) Foreign Application Priority Data

Jun. 30, 2006    (GB) .................................. 0613161.9

(51) Int. Cl.

| A61K 9/00 | (2006.01) |
|---|---|
| A61K 9/14 | (2006.01) |
| A61K 9/16 | (2006.01) |
| A61K 31/40 | (2006.01) |
| A61K 45/06 | (2006.01) |
| A61K 47/12 | (2006.01) |

(52) U.S. Cl.
CPC .......... *A61K 9/1617* (2013.01); *A61K 9/0075* (2013.01); *A61K 9/145* (2013.01); *A61K 9/1688* (2013.01); *A61K 31/40* (2013.01); *A61K 45/06* (2013.01); *A61K 47/12* (2013.01)

(58) Field of Classification Search
None
See application file for complete search history.

(56) References Cited

U.S. PATENT DOCUMENTS

| 6,521,260 B1 | 2/2003 | Staniforth |
|---|---|---|
| 6,645,466 B1 | 11/2003 | Keller et al. |
| 6,884,794 B2 | 4/2005 | Staniforth et al. |

FOREIGN PATENT DOCUMENTS

| WO | WO 2000/33789 | 6/2000 |
|---|---|---|
| WO | WO 2001/76575 | 10/2001 |
| WO | WO 2002/00197 | 1/2002 |
| WO | WO 2002/43701 | 6/2002 |
| WO | WO 2004/093848 | 11/2004 |
| WO | WO 2005/025535 | 3/2005 |
| WO | WO 2005/025536 | 3/2005 |
| WO | WO 2005/025540 | 3/2005 |
| WO | WO 2005/025541 | 3/2005 |
| WO | WO 2005/025550 | 3/2005 |
| WO | WO 2005/041921 | 5/2005 |
| WO | WO 2005/046636 | 5/2005 |
| WO | WO 2005/105043 | 11/2005 |
| WO | WO 2005/107873 | 11/2005 |
| WO | WO 2007/068443 | 6/2008 |

OTHER PUBLICATIONS

Begat P et al. "The Influence of force Control Agents on the Cohesive-Adhesive Balance in Dry Powder Inhaler Formulations", KONA No. 23, pp. 109-121 (2005).

Ticehurst M D et al. "Characterisation of the influence of microisation on the crystallinity and physical stability of revatropate hydrobromide", International Journal of Pharmaceuticals, 193, pp. 247-259 (2000).

Ferrari F et al. "The Surface Roughness of lactose particles Can be Modulated by Wet-Smoothing Using a High-Shear Mixer", AAPS PharmSciTech, 5(4) Art. 80. pp. 1-6 (2004).

*Primary Examiner* — Leslie A. Royds Draper
(74) *Attorney, Agent, or Firm* — Daniel Woods

(57) ABSTRACT

A process for preparing dry powder formulations of a glycopyrronium salt for inhalation that have good stability. The process involves (a) micronising a glycopyrronium salt together with an anti-adherent agent, and (b) admixing carrier particles to form the dry powder formulation.

6 Claims, No Drawings

COMPOSITIONS OF GLYCOPYRRONIUM SALT FOR INHALATION

This invention relates to organic compounds and their use as pharmaceuticals, or more specifically a process for preparing dry powders of glycopyrronium salts.

Glycopyrronium bromide i.e. 3-[(cyclopentyl-hydroxyphenylacetyl)oxy]-1,1-dimethyl-pyrrolidinium bromide but also known as glycopyrrolate is an antimuscarinic agent that is currently administered by injection to reduce secretions during anaesthesia and or taken orally to treat gastric ulcers. It has the following chemical structure:

and can be prepared using the procedure described in United States patent U.S. Pat. No. 2,954,062.

Schroeckenstein et al. *J. Allergy Clin. Immunol.* 1998; 82(1):115-119 discloses the use of glycopyrrolate in an aerosol formulation for treating asthma where a single administration of a metered dose achieved bronchodilation for up to 12 hours.

It is known that quaternary ammonium compounds with antimuscarinic activity tend to agglomerate during storage. For example, Ticehurst et al, *International journal of Pharmaceutics* 193 (2000) pages 247-259 observes this in micronised revatopate hydro-bromide. This problem affects the physical and chemical stability of the drug substance and its performance in formulations.

International patent application WO 2001/76575 discloses glycopyrrolate can be formulated as a dry powder for pulmonary delivery in controlled release formulation. In the example micronised glycopyrrolate is mixed with magnesium stearate in the ratio of 75:25 by mass and that mixture is ball milled and dried to give a dry powder.

International patent application WO 2005/25536 discloses a method for making composite active particles for use in a pharmaceutical composition for pulmonary inhalation that involves jet milling active particles with certain additive materials to enhance fine particle fraction and fine particle dose.

It has now been found, surprisingly, that it is advantageous to miconise a glycopyrronium salt together with an anti-adherent agent and then admix carrier particles as this reduces the tendency for the resulting drug substance to agglomerate and therefore improves the stability of the resulting drug substance.

Accordingly in broad terms the present invention provides a process for preparing dry powder formulations of a glycopyrronium salt for inhalation that comprises the steps of (a) micronising a glycopyrranium salt together with an anti-adherent agent, and (b) admixing carrier particles to form the dry powder formulation.

Processing the glycopyrronium salt in this way reduces the tendency for the resulting drug substance to agglomerate, a commonly known behaviour of micronized quaternary ammonium compounds particularly when stored in humid conditions or otherwise exposed to moisture.

Preferably the glycopyrronium salt is glycopyrrolate.

Preferably the glycopyrronium salt and the anti-adherent agent are pre-mixed to give a homogeneous blend before being micronised together.

Preferably the anti-adherent agent is one or more metal stearates, one or more crystalline sugars or a mixture thereof. Especially preferred metal stearates include magnesium stearate and calcium stearate. Especially preferred crystalline sugars include lactose, more especially lactose monohydrate or anhydrous lactose.

When the anti-adherent agent is a metal stearate, the glycopyrronium salt is suitably micronised with from 1 to 20% by mass of the anti-adherent agent, more preferably from 2 to 10% by mass of the anti-adherent agent, but most preferably from 3 to 5% by mass of the anti-adherent agent.

When the anti-adherent agent is a crystalline sugar, the crystalline sugar is suitably micronised with the glycopyrronium salt in a ratio of from 0.5:1 to 10:1 by mass, more preferably from 1:1 to 5:1 by mass, but most preferably from 2:1 to 3:1 by mass. Preferably the carrier particles are mixed with the micronised glycopyrronium salt and anti-adherent agent in a ratio of from 2000:1 to 5:1 by mass, especially from 200:1 to 20:1 by mass. The carrier particles are preferably crystalline sugars, for example lactose monohydrate or anhydrous lactose.

The glycopyrronium salt and the anti-adherent agent are optionally micronised together with one two, three or more additional active ingredients. Alternatively, the glycopyrronium salt and the anti-adherent agent and one or more additional active ingredients are micronised and the resulting product is mixed with one or more additional active ingredients that have already been micronised. In each case the or each additional active ingredient is suitably selected from the group consisting of anti-inflammatory, bronchodilatory, antihistamine, decongestant and anti-tussive drug substances.

Terms used in the specification have the following meanings:

"Glycopyrronium salt" as used herein is intended to encompass any salt form or counterion of glycopyrronium, including but not limited to glycopyrronium bromide (glycopyrrolate), glycopyrronium chloride, or glycopyrronium iodide, as well as any and all isolated stereoisomers and mixtures or stereoisomers thereof. Derivatives of glycopyrronium salts are also encompassed. Suitable counter ions are pharmaceutically acceptable counter ions including, for example, fluoride, chloride, bromide, iodide, nitrate, sulfate, phosphate, formate, acetate, trifluoroacetate, propionate, butyrate, lactate, citrate, tartrate, malate, maleate, ate, benzoate, p-chlorobenzoate, diphenyl-acetate or triphenylacetate, o-hydroxy-benzoate, p-hydroxybenzoate, 1-hydroxynaphthalene-2-carboxylate, 3-hydroxynaphthalene-2-carboxylase, methanesulfonate and benzene-sulfonate.

"Anti-adherent agent" as used herein means a material that reduce the cohesion between particles and prevents fine particles becoming attached to the inner surfaces of an inhaler device, or a mixture of such materials. Anti-adherent agents also include anti-friction agents or glidants, which give the powder formulation better flow properties in the inhaler. They usually lead to better dose reproducibility and higher fine particle fractions. Typical anti-adherent agents include amino acids such as leucine, phospholipids such as lecithin or fatty acid derivatives such as magnesium stearate or calcium stearate.

"Metered dose" or "MD" of a dry powder formulation as used herein is the total mass of active agent present in the metered form presented by the inhaler device in question. For example, the MD might be the mass of glycopyrronium salt present in a capsule for a particular dry powder inhaler, or in a foil blister for use in a particular dry powder inhaler device.

"Emitted dose" or "ED" as used herein is the total mass of the active agent emitted from the device following actuation. It does not include the material left inside or on the surfaces of the device. The ED is measured by collecting the total emitted mass from the device in an apparatus frequently referred to as a dose uniformity sampling apparatus (DUSA), and recovering this by a validated quantitative wet chemical assay.

"Fine particle dose" or "FPD" as used herein is the total mass of active agent which is emitted from the device following actuation which is present in an aerodynamic particle size smaller than a defined limit. This limit is generally taken to be 5 µm if not expressly stated to be an alternative limit, such as 1 µm or 3 µm, etc. The FPD is measured using an impactor or impinger, such as a twin stage impinger (TSI), multi-stage Liquid impinger (MSLI), Andersen Cascade Impactor (ACI) or a Next Generation Impactor (NGI). Each impactor or impinger has a predetermined aerodynamic particle size collection cut-off point for each stage. The FPD value is obtained by interpretation of the stage-by-stage active agent recovery quantified by a validated quantitative wet chemical assay where either a simple stage cut is used to determine FPD or a more complex mathematical interpolation of the stage-by-stage deposition is used.

"Fine particle fraction" or "FPF" as used herein is normally defined as the FPD divided by the ED and expressed as a percentage. Herein, the FPF of ED is referred to as FPF(ED) and is calculated as FPF(ED)=(FPD/ED)×100%. "Fine particle fraction" may also be defined as the FPD divided by the MD and expressed as a percentage. Herein, the FPF of MD is referred to as FPF(MD), and is calculated as FPF(MD)=(FPD/MD)×100%.

Throughout this specification and in the claims that follow, unless the context requires otherwise, the word "comprise", or variations such as "comprises" or "comprising", will be understood to imply the inclusion of a stated integer or step or group of integers or steps but not the exclusion of any other integer or step or group of integers or steps.

The present invention provides a process for preparing dry powder formulations of a glycopyrronium salt.

Dry powder formulations for inhalation in the treatment of respiratory diseases are generally formulated by mixing a micronised active pharmaceutical ingredient with coarse carrier particles to give to an ordered mixture. The carrier particles make the micronised active pharmaceutical ingredient less cohesive and improve its flowability. This makes the powder easier to handle during the manufacturing process. The micronised active particles tend to adhere to the surface of the carrier particles when stored in a dry powder inhaler device but are dispersed from the surfaces of the carrier particles on inhalation into rise respiratory tract to give a fine aerosol. The larger carrier particles are mostly deposited in the oropharyngeal cavity.

In recent years certain chemical compounds such as magnesium stearate (which is sometimes referred to as a "force control agents") have been included in dry powder formulations for inhalation. For example, Unites States parent U.S. Pat. No. 6,645,466 discloses the use of magnesium stearate in dry powder formulations for inhalation to improve moisture resistance and storage stability. And United States patent U.S. Pat. No. 6,528,096 discloses the use of a lubricant such as magnesium stearate in dry powder formulations for inhalation to provide ordered stable mixtures without segregation of the active particles during handling and before use. Such dry powder formulations for inhalation are commonly prepared by mixing carrier particles and magnesium stearate to give a preliminary mixture or blend of magnesium stearate coated carrier particles, then admixing active particles to give the desired formulation.

In contrast to that it has now been found, surprisingly, that it is advantageous to micronise a glycopyrronium salt together with an anti-adherent agent, for example magnesium stearate or lactose monohydrate, and then admix carrier particles. That reduces the tendency for the resulting micronised glycopyrronium salt to agglomerate, which is a problem that is commonly observed in micronised quaternary ammonium derivatives. The process of the invention minimises dosing and delivery problems associated with agglomeration. It also enhances stability of the micronised glycopyrronium salt, which makes handling of the drug substance much easier and significantly enhances storage stability under various storage conditions (e.g. 25° C./60% relative humidity (RH), 30° C./75% RH).

The present invention provides a process for preparing dry powder formulations of a glycopyrronium salt for inhalation that comprises the steps of (a) micronising a glycopyrronium salt together with an anti-adherent agent, and (b) admixing carrier particles to form the dry powder formulation.

In the first step (a) a glycopyrronium salt and an anti-adherent agent are micronised together or "co-micronised". This, in general terms, provides pulverising the glycopyrronium salt and an anti-adherent agent using mechanical means such that at least 90% but preferably at least 95% of the resulting particulate material has an average particle size that is less than about 7 microns in diameter.

Glycopyrrolate is commercially available or may be prepared using the method described in U.S. Pat. No. 2,956,062. It is preferably crystalline and contains minimal amorphous parts.

Glycopyrrolate has two stereogenic centres and hence exists in four isomeric forms, namely (3R,2'R)-, (3S,2'R)-, (3R,2'S)- and (3S,2'S)-3-[(cyclopentyl-hydroxyphenylacetyl)oxy]-1,1-dimethylpyrrolidinium bromide, as described in United States patent specifications U.S. Pat. Nos. 4,530,7060 and 6,613,795. The contents of these patent specifications are incorporated herein by reference. The present invention embraces using one or more of these isomeric forms, especially the 3S,2')R isomer, the 3R,2'R isomer or the 2S,3'R isomer, thus including single enantiomers, mixtures of diastereomers, or racemates, especially (3S,2'R/3R,2'S)-3-[(cyclopentyl-hydroxy-phenylacetyl) oxy]-1,1-dimethylpyrrolidinium bromide.

The anti-adherent agent reduces the cohesion between particles and stabilizes activated surfaces from glycopyrrolate, thus preventing fine particles becoming agglomerated. It provides a general stabilization of the particle size distribution of the micronised materials and thus improves the stability of the final dry powder blends with the carrier agent. Furthermore it enhance the stability of the micronised material upon handling and storage significantly Suitable anti-adherent agents include fatty acid derivatives including metal stearates such calcium stearate and magnesium stearate; crystalline sugars including monosaccharides, disaccharides, polysaccharides and sugar alcohols such as arabinose, glucose, fructose, ribose, mannose, sucrose, trehalose, lactose, maltose, starches, dextran, marmitel or sorbitol, especially lactose, but particularly lactose monohydrate or anhydrous lactose; amino acids such as leucine, phospholipids such as lecithin; sodium stearyl fumarate; sodium stearyl lactylate; phospharidylcholines, phospharidylglycerols and other examples of natural and synthetic lung surfactants; liposomal formulation; lauric acid and its salts, for example, sodium lauryl sulphate, magnesium lauryl sulphate; triglycerides such as Dynsan 118 and Cutina HR; sugar esters in general; or a mixture of any such compounds. Preferably the anti-adherent agent is magnesium stearate, calcium stearate, lactose monohydrate, anhydrous lactose or a mixture thereof. The anti-adherent agent is most preferably magnesium stearate.

The anti-adherent agent is preferably in particulate form.

Where necessary or useful, the glycopyrronium salt and/or the anti-adherent agent are sieved prior to co-micronising.

In a preferred embodiment the glycopyrronium salt is mixed with the anti-adherent agent (or mixture of anti-adherent agents) to give a homogeneous blend prior to being co-micronised.

The glycopyrronium salt is suitably micronised with from 1 to 20% by mass of the anti-adherent agent, more preferably from 2 to 10% by mass of the anti-adherent agent, but most preferably from 3 to 5% by mass of the anti-adherent agent.

Micronising reduces the particle size of the glycopyrronium salt to a size that is suitable for administration by inhalation. The mass median aerodynamic diameter (MMAD) of these particles is preferably less than 10 microns (μm). Particles having aerodynamic diameters greater than about 10 μm are likely to impact the walls of the throat and generally do not reach the lung. Particles having aerodynamic diameters in the range of about 2. μm to about 5 μm will generally be deposited in the respiratory bronchioles whereas smaller particles having aerodynamic diameters in the range of about 0.0.5 μm to about 2 μm are likely to be deposited in the alveoli and to be absorbed into the bloodstream.

Co-micronising a glycopyrronium salt with an anti-adherent agent, especially magnesium stearate or lactose monohydrate, significantly reduces the micronised drug substance forming aggregates/agglomerates. Particles of the anti-adherent agent form a layer on the glycopyrronium salt particles that reinforce the desired effects of the anti-adherent agent, e.g. by reducing the tendency of the particles to agglomerate, particularly when exposed to humid conditions. The anti-adherent agent thus increases the physical stability of the micronised glycopyrronium salt particles. This overcomes or at least improves the problem of obtaining a suitable and stable fine particle fraction (FPF), which is commonly seen when formulating antimuscarinic agents. Overcoming this problem improves the stability during handling of the micronised drug substance (e.g. during preparation of the dry powder, blend), improves the storage stability of the micronised drug substance, improves the storage times (shelf live) of the glycopyrronium salt and enhances the dosing efficiency of dry powder formulations administered by pulmonary inhalation by stabilizing physicochemical properties (i.e. particle size distribution of drug substance).

Micronising equipment is well known in the art and includes a variety of grinding and milling machinery, for example compressive-type mills such as mechanofusion mills, impact mills such as ball mills, homogenizers and microfluidizers, and jet mills. In a preferred embodiment crystalline glycopyrronium salt is jet milled in a Hosokawa Alpine® 100 AFG fluid bed apposed jet mill. Other suitable jet milling equipment includes Hosokawa Alpine® AFG140, AFG200, AFG280 and AFG400 jet mills.

Suitable mixing equipment for any initial blending of the anti-adherent agent and the glycopyrronium salt includes low shear mixers such as a Turbula® powder blender and high-shear mixers such as a MiPro® powder blender.

In the second step (b) of the process of the present invention carrier particles are admixed with the co-micronised glycopyrronium salt and anti-adherent agent to form the dry powder formulation.

Preferably the carrier particles are mixed with the micronised glycopyrronium salt and anti-adherent agent in a ratio of from 2000:1 to 5:1 by mass, especially from 200:1 to 20:1 by mass.

The carrier particles may be composed of any pharmacologically inert material or combination of materials which is acceptable for inhalation. They are suitably composed of one or more crystalline sugars including monosaccharides, disaccharides, polysaccharides and sugar alcohols such as arabinose, glucose, fructose, ribose, mannose, sucrose, trehalose, lactose, maltose, starches, dextran, mannitol or sorbitol. An especially preferred carrier is lactose, for example lactose monohydrate or anhydrous lactose.

Preferably substantially all (by weight) of the carrier particles have a diameter of 20 to 1000 pm, more preferably 50 to 500 μm, but especially 20 to 250 μm. The diameter of substantially all (by weight) of the carrier particles is suitably less than 355 μm. This provides good flow and entrainment characteristics and improved release of the active particles in the airways to increase deposition of the active particles in the lower lung. It will be understood that, throughout, the diameter of the particles referred to is the aerodynamic diameter of the particles.

Where necessary or useful, the dry powder obtained by step (b) is subjected to a final size reduction so that the dry powder meets desired physical properties.

In an alternative aspect of the present invention the glycopyrronium salt and the anti-adherent agent are micronised together with at least one (preferably one, two or three) additional active ingredient to give a fixed dose combination. That or each additional active ingredient is preferably selected from the group consisting of anti inflammatory, bronchodilatory, antihistamine, decongestant and anti-tussive drug substances that are suitable for administration by inhalation, for example for the treatment of a respiratory disease. The or each additional active ingredient is most preferably selected from the group consisting of $\beta_2$-adrenoceptor agonists, antimuscarinic agents, steroids, PDE4 inhibitors, $A_2$, agonists and calcium blockers.

Suitable $\beta_2$-adrenoceptor agonists include albuterol (salbutamol), metaproterenol, terbutaline, salmeterol, fenoterol, indacaterol, procaterol, and especially, formoterol, carmoterol, TA-2005, GSK159797 and pharmaceutically acceptable salts thereof, and also compounds of EP 1440966, EP 1460064, EP 1477167, JP 05025045, US 2002/0055651, US 2004/0242622, US 2004/0229904, US 2005/0133417, US 2005/5159448, WO 93/18007, WO 99164035, WO 00/75114, WO 01/42193, WO 01/83462, WO 02/66422, WO 02/70490, WO 02/76933, WO 03/24439, WO 03/42160, WO 03/42164, WO 03/72539, WO 03/91204, WO 03/99764, WO 04/16578, WO 04/16601, WO 04/22547, WO 04/32921, WO 04/33412, WO 04/37768, WO 04/37773, WO 04/37807, WO 04/39762, WO 04/39766, WO 04/45618 WO 04/46083, WO 04/80964, WO 04/087142, WO 04/089892, WO 04/108675, WO 04/108676, WO 05/033121, WO 05/040103, WO 05/044787, WO 05/058867, WO 05/065650, WO 05/066140, WO 05/07908, WO 05/74924, WO 05/77361, WO 05/90288, WO 05/92860, WO 05/92887, WO 05/90287, WO 05/95328, WO 05/102350, WO 06/56471, WO 06/74897 and WO 06/08173.

Suitable bronchodilatory drugs include anticholinergic or antimuscarinic agents, in particular ipratropium bromide, oxitropium bromide, tiotropium salts, CHF 4226 (Chiesi) and SVT-40776, but also those described in EP 424021, U.S. Pat. No. 3,714,357, U.S. Pat. No. 5,171,744, US 2005/171147, US 2005/182091, WO 01/04118, WO 02/00652, WO 02/51841, WO 02153564, WO 03/00840, WO 03/33495, WO 03/53966, WO 03/87094, WO 04/018422, WO 04/05285, WO 05/077361 and WO 06/48225.

Suitable dual anti-inflammatory and bronchodilatory drugs include dual $\beta_2$-adrenoceptor agonist/muscarinic antagonists such as those disclosed in US 2004/0167167, US 2004/02426422, US 2003/182092, US 2005/256114, US 2006/35933, WO 04/74246, WO 04/74812, WO 04/89892 and WO 06/23475.

Suitable steroids include glucocorticosteroids such as budesonide, bechimethasone, fluticasone, ciclesonide or mometasone, or those described in WO 02/88167, WO 02/12266, WO 02/100879 or WO 02/00679, especially those of Examples 3, 11, 14, 17, 19, 26, 34, 37, 39, 51, 60, 67, 72, 73, 90, 99 and 101, and non-steroidal steroid agonists such as those described in WO 00/00531, WO 02/10143, WO 03/082280, WO 03/082787, WO 03/104195 and WO 04/005229.

Suitable PDE4 inhibitors include cilomilast (Ariflo® GlaxoSmithKline), Roflumilast (Byk Gulden), V-11294A (Kapp), BAY19-8004 (Bayer), SCH-351591 (Schering-Plough), Arofylline (Almirall Prodesfarma), PD189659/PD168787 (Parke-Davis), AWD-12-281 (Asta Medical), CDC-801 (Celgene), KW-4490 (Kyowa Hakko Kogyo), VM554/UM565 (Vernalis), T-440 (Tanabe), KW-4490 (Kyowa Hakko Kogyo) and GEC 3886 (Oglemilast, Glenmark), but also those described in WO 92/19594, WO 93/19749, WO 93/19750, WO 93/19751, WO 98/18796, WO 99/16766, WO 01/13953, WO 03/39544, WO 03/104204, WO 03/104205, WO 04/000814, WO 04/000839 and WO 04/005258, WO 04/018450, WO 04/018451, WO 04/018457, WO 04/018465, WO 04/018431, WO 041018449, WO 04/018450, WO 04/018451, WO 04/018457, WO 04/018465, WO 04/019944, WO 04/019945, WO 04/045607, WO 04/037805, WO 04/063197, WO 04/103998, WO 04/111044, WO 05/012252, WO 05/012253, WO 05/013995, WO 05/030212, WO 05/030725, WO 05/087744, WO 05/087745, WO 05/087749 and WO 05/090345.

Suitable A2a agonists include those described in EP 409595A2, EP 1052264, EP 1241176, WO 94/17090, WO 96/02543, WO 96/02553, WO 98/28319, WO 99/24449, WO 99/24450, WO 99/24451, WO 99/38877, WO 99/41267, WO 99/67263, WO 99/67264, WO 99/67265, WO 99/67266, WO 00/23457, WO 00/77018, WO 00/78774, WO 01/23399, WO 01/27130, WO 01/27131, WO 01/60835, WO 01/94368, WO 02/00676, WO 02/22630, WO 02/96462, WO 03/086408, WO 04/039762, WO 04/039766, WO 04/045618 and WO 04/046083.

Suitable calcium channel bloaters include dilriazem, verapamil, amlodipine, felodipine, isradipine, lacidipine, lercanidipine, nicardipine, nifedipine, nimodipine and nisoldipine.

In a preferred embodiment the or each additional active ingredient is salmeterol, indacaterol or momerasone.

Preferred triple combinations contain glycopyrronium bromide, salmeterol and mometasone; glycopyrronium bromide, indacaterol and momerasone; glycopyrronium bromide, salmeterol and ciclesonide; glycopyrronium bromide, indacaterol and ciclesonide; glycopyrronium bromide, salmeterol and 3-methyl-thiophene-2-carboxylic acid (6S,9R,10S,11S,13S,16R, 17R)-9-chloro-6-fluoro-11-hydroxy-17-methoxycarbonyl-10,13,16-trimethyl-3-oxo-6,7,8, 9,10,11,12,13,14,15,16,17-dodeca-hydro-3H-cyclopenta[a]phenanthren-17-yl ester; or glycopyrronium bromide, indacaterol and 3-methyl-thiophene-2-carboxylic acid (6S, 9R,10S, 11S,13S,16R,17R)-9-chloro-6-fluoro-11-hydroxy-17-methoxycarbonyl-10,13,16-trimethyl-3-oxo-6,7,8,9,10,11,12,13,14,15,16,17-dodeca-hydro-3H-cyclopenta[a]phenanthren-17-yl ester.

The dry powder of the present invention may be contained as unit doses in capsules of, for example, gelatin or hydroxypropylmethyl cellulose (HPMC), or in blisters (e.g. of aluminium or plastic), for use in a dry powder inhalation device, which may be a single dose or multi-dose device. Preferably the total weight of powder per capsule or premetered unit is from 2 mg to 50 mg. Alternatively, the dry powder may be contained in a reservoir in a multi-dose dry powder inhalation (MDDPI) device adapted to deliver, for example, 3-25 mg of dry powder per actuation. A suitable device for delivery of dry powder in encapsulated form is described in U.S. Pat. No. 3,991,761 (including the AEROLIZER™ device) or WO 05/113042, while suitable MDDPI devices include those described in WO 97/20589 (including the CERTIHALER™ device), WO 97/30743 (including the TWISTHALER™ device) and WO 05/37353 (including the GYROHALER™ device).

The invention is illustrated by the following Examples.

EXAMPLES

Example 1

37 g of magnesium smarm are mixed with 1 kg of crystalline glycopyrronium bromide in a Turbula® blender for 5 hours. The resulting mixture is micronised using a Hosokawa Alpine® 100 AFG fluid bed opposed jet mill with the following parameters: classifier speed, 13000 rpm; milling gas pressure, 3.5 bar. The mill is equipped with 3 nozzles of 1.9 mm diameter.

The resulting mixture has a median particle size of about 3 micron (x90=7 micron, x50=3 micron, x10=1 micron). The magnesium stearate is well distributed over the drug substance surface.

Lactose carrier particles (99.7% w/w of final composition) are admixed to give an inhalable dry powder.

Example 2

Drug substance 1:50 g of magnesium stearate are mixed with 1 kg of crystalline glycopyrronium bromide in a Turbula® blender for 5 hours. The resulting mixture is micronised using a Hosokawa Alpine® 100 AFG fluid bed opposed jet mill (equipped with 3 nozzles of 1.9 mm diameter) with the following parameters: classifier speed, 13000 rpm; milling gas pressure, 3.5 bar, to give particles that have an average particle size of less than 5 microns.

Drug substance 2: 1 kg of crystalline glycopyrroninum bromide is micronised using a Hosokawa Alpine® 100 AFG fluid bed opposed jet mill (equipped with 3 nozzles of 1.9 mm diameter) with the following parameters: classifier speed, 13000 rpm; milling gas pressure, 3.5 bar, to give particles that have an average particle size of less than 5 microns.

These drug substances are used to prepare the following formulations:

Formulation 1: Lactose carrier particles (99 w/w of final composition) are admixed with drug substance 2 to give an inhalable dry powder.

Formulation 2: Lactose carrier particles (98.8 w/w, of final composition) and magnesium stearate (0.15%) are admixed with drug substance 2 to give an inflatable dry powder.

Formulation 3: Lactose carrier particles (98.8 w/w of final composition) and magnesium stearate (0.15%) are admixed with drug substance 1 to give an inhalable dry powder.

The resulting powders are filled in aliquots of 25 mg into size 3 hydroxypropylmethyl-cellulose (HPMC) capsules. The resulting capsules are tested for aerodynamic particle size distribution (fine particle fraction) either immediately after manufacture or after storage under different conditions as outined in Table 3 below.

The fine particle fraction (FPF) and emitted dose (ED) of the powder in each capsule is measured using the Next Generation Impactor (NGI) particle-classifying cascade impactor at a flow rate of 85 L/min. The fine particle fraction relative to the emitted dose FPF(ED) of the various samples is shown in Table 1 below. The relative change in FPF(ED) as compared from initial is also shown in that Table.

TABLE 1

| Sample | Formulation | Testing timepoint and condition of drug substance | FPF (ED) [%] | Change from initial [%] |
|---|---|---|---|---|
| 1 | Formulation1 | Initial testing (drug substance 2) | 51.5 | — |
| | | 6 weeks 30° C./65% RH | 46.3 | −10.1 |
| | | 6 weeks 40° C./75% RH | 32.2 | −37.5 |
| 2 | Formulation 2 | Initial testing (drug substance 2) | 50.5 | — |
| | | 6 weeks 30° C./65% RH | 43.7 | −13.5 |
| | | 6 weeks 40° C./75% RH | 38.4 | −24.0 |
| 3 | Formulation 3 | Initial testing (drug substance 1) | 60.5 | — |
| | | 6 weeks 30° C./65% RH | 57.4 | −5.0 |
| | | 6 weeks 40° C./75% RH | 46.5 | −23.1 |

These data show that co-micronising glycopyrronium bromide with an anti-adherent agent improves the stability of the resulting drug substance as shown by a less marked decrease in the FPF over the storage period. The co-micronisation with the anti-adherent agent stabilises the FPF during storage compared to mixtures without anti-adherent agent and blends that have the magnesium stearate added during blending.

The invention claimed is:

1. A process for preparing a dry powder formulation of a glycopyrronium salt for inhalation that comprises the steps of (a) mixing a glycopyrronium salt and 3 to 5% by mass of magnesium stearate, based on the total amount of glycopyrronium salt and magnesium stearate, to give a homogeneous blend; (b) micronising the blend; and (c) admixing carrier particles to the micronized blend to form a dry powder formulation, wherein the carrier particles are mixed with the blend of micronized glycopyrronium salt and magnesium stearate in a ratio of 200:1 to 20:1 by mass.

2. A process according to claim 1 wherein the carrier particles are crystalline sugars.

3. A process according to claim 1 wherein the glycopyrronium salt is glycopyrronium bromide, glycopyrronium chloride or glycopyrronium iodide.

4. A process according to claim 3 wherein the glycopyrronium salt is glycopyrronium bromide.

5. A process according to claim 1 in which the blend of glycopyrronium salt and the magnesium stearate are micronised together with an additional active ingredient.

6. A process according to claim 5 in which the additional active ingredient is selected from the group consisting of salmeterol, indacaterol and mometasone.

* * * * *